United States Patent
Neuberger et al.

(10) Patent No.: US 6,421,361 B1
(45) Date of Patent: Jul. 16, 2002

(54) TUNABLE DIODE LASER SYSTEM FOR PHOTODYNAMIC THERAPY

(75) Inventors: Wolfgang Neuberger, F.T. Labaun (MY); Stefan Spaniol, Bonn (DE)

(73) Assignee: CeramOptec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/337,952

(22) Filed: Jun. 22, 1999

(51) Int. Cl.$^7$ ................................................. H01S 3/10
(52) U.S. Cl. ............................ 372/20; 372/34; 372/98; 372/32
(58) Field of Search ............................. 372/75, 69, 34, 372/20, 63, 64, 98, 32

(56) References Cited

U.S. PATENT DOCUMENTS

| | | | | |
|---|---|---|---|---|
| 4,573,159 A | * | 2/1986 | Aagano et al. | 372/34 |
| 4,697,269 A | * | 9/1987 | Ohara | 372/34 |
| 4,791,634 A | * | 12/1988 | Miyake | 372/34 |
| 4,953,176 A | * | 8/1990 | Ekstrand | 372/34 |
| 5,175,643 A | | 12/1992 | Andrews | |
| 5,353,293 A | * | 10/1994 | Shull | 372/34 |
| 5,550,853 A | * | 8/1996 | Ostler | 372/34 |
| 5,668,803 A | | 9/1997 | Neuberger | |
| 5,771,325 A | | 6/1998 | Neuberger | |
| 5,875,206 A | * | 2/1999 | Chang | 372/75 |
| 6,069,907 A | * | 5/2000 | Chang | 372/75 |
| 6,181,718 B1 | * | 1/2001 | Kobayashi et al. | 372/34 |

\* cited by examiner

Primary Examiner—Leon Scott, Jr.
(74) Attorney, Agent, or Firm—Bolesh J. Skutnik; B J Associates

(57) ABSTRACT

A tunable medical laser diode system for activating Photo-Dynamic Therapy (PDT) compounds is disclosed. A tunable medical laser diode system for activating PhotoDynamic Therapy (PDT) compounds and other moderate or low energy multiple wavelength applications is disclosed. Interchangeable diode laser cartridges are used. Each cartridge contains a diode laser, which consists of at least one diode or diode array or some combination thereof. Typically, each diode laser cartridge is tuned to a different wavelength. Multiple cartridges, however may be tuned to the same wavelength for some applications One or more cartridges are attached to the system base unit simultaneously. The cartridges may be powered in series or in tandem for different applications. Selectively powering these cartridges causes light to be emitted at a certain wavelength or wavelengths. Selection of cartridges is facilitated by a drug identification scanner which scans drug activation wavelength information into the system. The wavelength can then be changed by selecting different cartridge(s) with diodes operating at other wavelengths. Applicator fiber parameters are recognized by the system as are power output and energy density. Modifications of input power are made accordingly. On a finer scale, tuning can be accomplished using a Master Oscillator Power Amplifier (MOPA). Still Finer tuning can be done by adjustment of system operating temperature. The ability to vary output wavelengths allows for multiple PDT compounds to be activated by one laser system. Other medical applications, such as aiding coagulation, may also be performed with diode lasers using the present invention, while retaining the inherent advantages of diode lasers, i.e., simplicity, low cost, and ease of maintenance.

12 Claims, 4 Drawing Sheets

TUNABLE DIODE LASER SYSTEM FOR PHOTODYNAMIC THERAPY

BACKGROUND OF INVENTION

1. Field of the Invention

The field of this invention is diode laser systems for medical applications, in particular, tunable diode systems with interchangeable laser diode cartridges and recognition capabilities.

2. Invention Disclosure Statement

PhotoDynamic Therapy (PDT) is the activation of a pharmaceutical agent in the human body by a selected dose of a selected wavelength of radiation. PDT is gaining importance both for cancer and non-cancer applications. Typically, this therapy begins with the application of a photosensitizer (photoactive drug) that may be orally ingested, topically applied, injected, or intravenously introduced to a treatment site. After a suitable time interval depending on certain properties of the photosensitizer, radiation energy in a suitable wavelength band is selectively applied for a predetermined duration and intensity to the target site.

The basic concept of PDT is that certain molecules function as photosensitizers that absorb light of certain wavelengths. If light energy of the proper wavelength is delivered to the photosensitizer, it stores the energy from the photons by increasing its energy to a higher level called a triplet state. Inside the human body, some of the excited photosensitizer molecules transfer the stored energy to nearby oxygen molecules, exciting them to a higher energy level called a singlet state. Singlet oxygen is a highly reactive molecule that rapidly oxidizes essential cellular components that surround it, and in a living cell this oxidation causes necrosis.

PDT is a desirable form of treatment because it allows for treatment of very extensive tumors and growths without damaging healthy tissue to the extent of chemotherapy or radiation therapy. Most commonly, photosensitizers used in PDT consist of a hematoporphyrin derivative (HpD) such as porfimer sodium, or Photofrin. Although the mechanism of HpD's preferential location in malignant cells is uncertain, the total time that the derivatives are retained in the malignant tissue is much longer than in nonmalignant tissue, where it generally clears within 24–72 hours. As a result, there is a "window" of time in which the physician can exploit the differences in HpD concentrations to cause selective photodegradation of malignant tissue.

After photosensitizer administration, a delay of 24–72 hours allows for HpD to be expelled from healthy tissue, and the malignant tissue is irradiated with visible red light tuned to approximately 630 nm. Shortly after administering treatment, the tumor becomes necrotic and, when effectively treated, the tumor becomes a nonpalpable scab that is usually sloughed off within a few days. A high therapeutic ratio and relative lack of morbidity have made PDT a very attractive form of therapy.

Lasers have traditionally provided the preferred form of optical radiation to activate photosensitizers. To be used in medical applications, however, photosensitizers must be approved by the FDA in conjunction with a laser system and/or laser wavelength. This means that hospitals and other end users must purchase a new and different laser system for each photosensitizer that it wishes to activate, unless the laser system is tunable. This is the reason that inexpensive diode lasers have not been used in PDT applications, i.e. because their wavelength is fixed. Therefore, primarily because of tunability, costly dye laser systems have traditionally been used in this application.

Dye laser systems possess the desirable characteristic of being continuously tunable over a very broad range to emit radiation at different wavelengths. Dye laser systems, however, have several critical disadvantages. In addition to being expensive, dye laser systems are inefficient, large, complicated in operation, and difficult to maintain. Dye lasers use a dye solution as the active medium. The problem that ensues is that the dye solution is consumed in the lasing process. To solve this problem, ways of replenishing the dye solution were developed, such as reservoirs and fluid transport systems. Such replenishment systems, however, are also problematic. Firstly, a dye laser system, including fluid transport, can require a great deal of space. In fact, entire rooms in hospitals are often dedicated to the operation of such systems. The fluid transport system also may be awkward in terms of emptying old fluid and adding new chemicals. Another problem with dye laser systems is that they are inefficient. This is due to a two-step power conversion process. First, electricity must be coupled with a high intensity light source to be converted into optical energy. Second, optical energy emitted from the high intensity light source must activate the dye solution before laser light is generated for practical use. These steps are lossy. As a result, dye laser systems use significantly more energy per output watt than diode laser systems. Also, dye laser systems have a shorter life span than diode lasers.

Diode lasers possess many advantages when compared to dye lasers. They are efficient, inexpensive, easy to operate and maintain, and compact. However, the wavelength emitted by a diode laser is practically fixed due to its composition, with only minor tuning possible through adjustment of operating temperature. For example, temperature tuning can give up to 5 nm of tuning range. But, to activate a broad range of PDT compounds, a tuning range of roughly 200 nm, from 630 nm to 800 nm, is necessary.

Thus, the ideal laser for PDT applications, and similar multiple wavelength applications, would offer the equivalent tunability of a dye laser, but in a compact solid state electronic package, as in a diode laser system, possibly with radiative or air cooling.

U.S. Pat. No. 5,771,325 entitled "Modular Laser Systems", invented by present inventor, Wolfgang Neuberger, and assigned to the Assignee of the present invention has some pertinent points in this area and is hereby expressly incorporated by reference as part of the present disclosure. This patent deals with diode laser systems and describes a system of interchangeable laser diode modules. In this system, laser diodes are contained in modules which can be easily interchanged. The goal of this invention was to create a more efficient, higher power laser, with reliable and stable output. Added efficiency came from having a low down time for repairs because of the ability to quickly replace nonfunctioning modules with working modules. Higher power resulted from having multiple diode modules of the same wavelength in operation simultaneously. Reliability and stability of output resulted from operating the laser system at lower than maximum current and the ability to operate the laser unit continuously despite the failure of one diode or diode array. Thus, this invention effectively treated power level and ease of serviceability of diode lasers, specifically relating to industrial applications. However, '325 does not address the real need of the present invention. The need addressed by the present invention is a tunable diode laser system for medical applications.

The '325 patent also describes a large system using a laser rod to combine laser power from multiple modules. Because of high power input levels, the invention in '325 also generates high temperature levels and therefore requires sizeable heat exchange apparatus.

The concept of modularity and easy replacement of diodes described by '325 may be useful for application to the problem addressed by the present invention. What is still lacking is how to create a diode laser system that is tunable. How to interchange diode modules of different wavelengths in a hospital or outpatient clinic setting must also still be addressed, as well as a desire to automate recognition of diode lasers available.

The process of interchanging diode modules or cartridges is inherently problematic. Coupling of laser diodes with optical fibers requires extreme precision. If the diode/fiber interface is slightly amiss, a malfunction will occur. Thus, to develop a system where the diode/fiber interface is continually being disconnected and reconnected because of interchanging cartridges requires great skill, or a very novel approach.

Recognition of drug activation wavelength and fiber characteristics by the laser system is also an area of needed improvement. What is needed is a system that can identify a drug, its wavelength, and poll the lasers in the system for a laser of the necessary wavelength. Such system would also read fiber characteristics to regulate power input.

It is therefore the aim of the present invention to provide a PDT diode laser system that provides for wavelengths to be changed by a simple process, while retaining the inherent advantages of diode lasers (simplicity, low cost, ease of maintenance).

SUMMARY AND OBJECTIVES

It is therefore an object of the present invention to provide a broadly tunable diode laser system used for the activation of PDT agents in the human body.

Another object of the present invention is to provide a diode laser system with wavelength tunability arising from the use of interchangeable diode laser cartridges.

Another object of the present invention is to provide a laser diode system capable of recognizing laser diodes, fiber parameters and other parameters such as output energy, and energy density.

Another object of the present invention is to provide a tunable diode laser system using a Master Oscillator Power Amplifier (MOPA).

Another objective of the present invention is to provide a tunable light source system where doctors or other medical personnel who have only minimal training in the operation of the apparatus may perform wavelength modification procedures.

Briefly stated, the present invention provides a tunable medical laser diode system for activating PhotoDynamic Therapy (PDT) compounds and other moderate or low energy multiple wavelength applications. Interchangeable diode laser cartridges are used. Each cartridge contains a diode laser, which consists of at least one diode or diode array or some combination thereof Typically, each diode laser cartridge is tuned to a different wavelength. Multiple cartridges, however may be tuned to the same wavelength for some applications One or more cartridges are attached to the system base unit simultaneously. The cartridges may be powered in series or in tandem for different applications. Selectively powering these cartridges causes light to be emitted at a certain wavelength or wavelengths. Selection of cartridges is facilitated by a drug identification scanner which scans drug activation wavelength information into the system. The wavelength can then be changed by selecting different cartridge(s) with diodes operating at other wavelengths. Applicator fiber parameters are recognized by the system as are power output and energy density. Modifications of input power are made accordingly. On a finer scale, tuning can be accomplished using a Master Oscillator Power Amplifier (MOPA). Still Finer tuning can be done by adjustment of system operating temperature. The ability to vary output wavelengths allows for multiple PDT compounds to be activated by one laser system. Other medical applications, such as aiding coagulation, may also be performed with diode lasers using the present invention, while retaining the inherent advantages of diode lasers, i.e., simplicity, low cost, and ease of maintenance.

The above, and other objects, features and advantages of the present invention will become apparent from the following detailed description read in conjunction with the accompanying drawings.

DETAILED DESCRIPTION OF PREFERRED EMBODIMENTS

The goal of the present invention is accomplished by quick-change cartridges containing one or more diodes or diode arrays of a specific wavelength. There are two fundamental units crucial to the operation of the invention; the diode cartridge and the base unit. A diode cartridge is similar to a typewriter ink cartridge in that it can be easily inserted and when it is inserted it is fixed in position by securing devices. Each diode cartridge contains a diode laser or diode laser array. The term "diode laser", used herein, includes, but is not limited to, laser diodes, super luminescent diodes and tapered laser diodes. Contained within each cartridge may be a planar wave-guide combiner, as described in U.S. Pat. No. 5,668,903, "Compound Laser System for High Power Densities" by inventor of the present invention, Wolfgang Neuberger, and assigned to the assignee of the present invention, which is hereby expressly incorporated by reference as part of the present disclosure. The combiner receives emissions from several separate laser components and transforms them into one compound beam. These components may be diodes or diode arrays. Use of the combiner provides for power densities to be maintained when multiple diode lasers are merged into one output source. Each cartridge has an optical port as a means of coupling with optical connections in the base unit. The cartridges also have a thermal contact for assisting heat transfer. Each cartridge has an electrical power port for connection to the power supply which is located within the base unit. Finally, each cartridge has a code identification port, or some other means, used to relay to the base unit the diode wavelength and other data for temperature adjustment, power requirements or other purposes.

The diode cartridge interfaces with the base unit. The base unit contains every part of the system that is not enclosed within the cartridge. Thus, the base unit includes an electrical power supply and a computer/controller for regulating the system. It also contains a heat dissipation means, e.g. a cooler and a fan, which is used for wavelength stability and can also be used for temperature tuning. Also contained in the base unit is an optical interface for fiber/applicator attachment and shutters, interlocks or other means to fulfill laser safety requirements. The base unit contains a drug identification scanner, or other means, which relays to the computer/controller the identification of the drug and the required wavelength to activate the drug. Also contained in the base unit is a means for identification of the treatment fiber. The base unit may also contain an optional calibration unit. All of the features of the base unit are encased within an enclosure.

Figure 1:
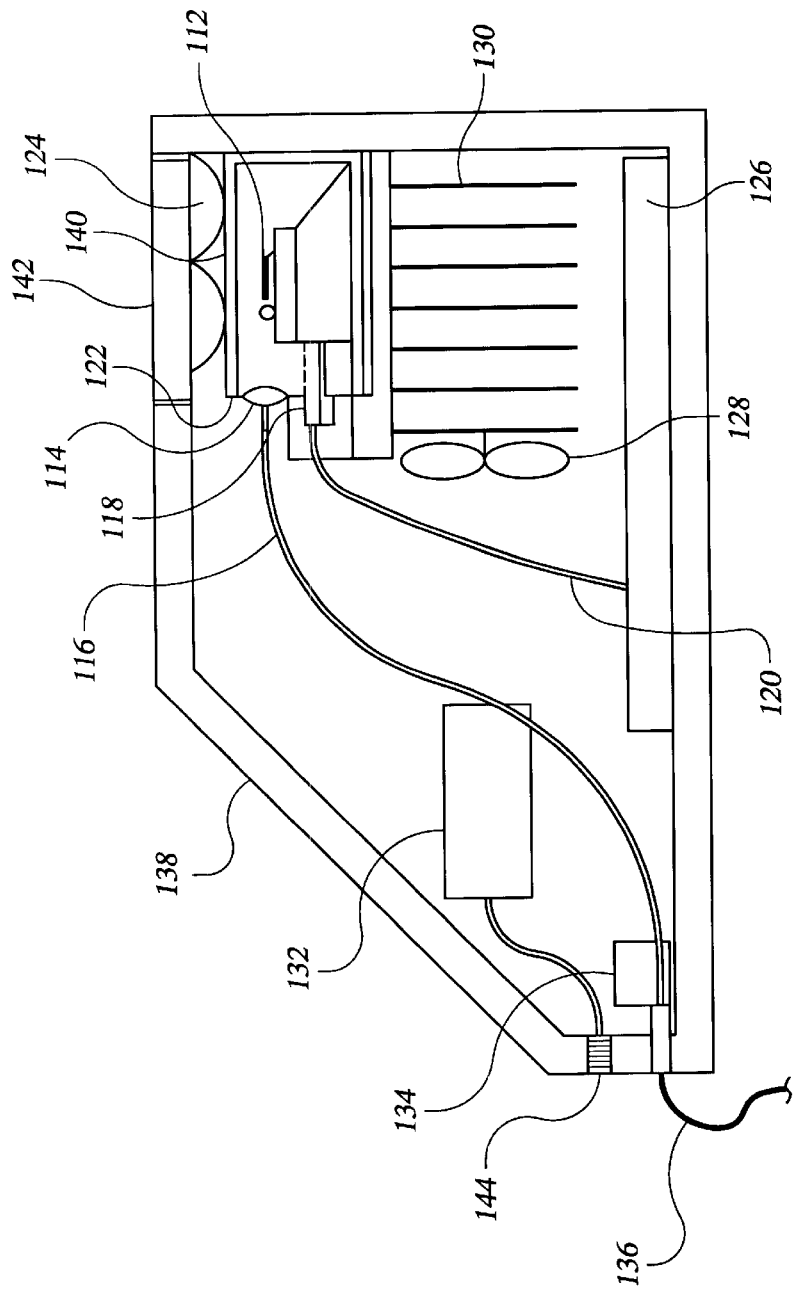
FIG. 1 is a schematic illustration of a tunable medical laser diode system for PDT according to the present invention.

FIG. 1 illustrates tunable laser diode system 100 according to the present invention, including base unit and at least one diode cartridge 140, which contains at least one diode laser 112. System 100 includes electrical connection 120 that connects electrical power supply 126, in base unit, to electrical port 118. Power is transmitted to selected diode cartridges 140 and diode lasers 112. Drug identification scanner 144 reads the drug information including the wavelength required to activate it into computer/controller 132. Computer/controller 132 then selectively powers the diode cartridge of the required wavelength. When a diode laser receives power it converts electrical energy into optical energy or light. The light then passes through optical port 114, optical connection 116 and shutter 134 into treatment fiber 136 for application to the human body.

EXAMPLE 1

Drug identification scanner 144 operates like a common bar code scanner. PDT drug A has a bar code on its container which identifies the drug and its activation wavelength. Drug identification scanner 144 scans the bar code (not displayed) and relays the information to computer/controller 132. Computer/controller 132 surveys the diode cartridges contained in the base unit to determine if a cartridge of the appropriate wavelength is available. Upon finding appropriate cartridge B, computer/controller 132 selectively powers cartridge B. Computer/controller 132 also collects data pertaining to the size and Numerical Aperture (NA) of treatment fiber 136 and regulates power supplied to cartridge B accordingly, so that radiation of the proper energy density is emitted at the output end of treatment fiber 136.

Fine tuning of emitted wavelength(s) is carried out by adjustment of operating temperature. Temperature adjustment can result in 5 nm of wavelength tuning. Increasing the operating temperature results in a shorter wavelength, whereas decreasing the operating temperature results in longer wavelength.

Diode laser 112 can be either a single laser diode emitter, or a laser diode array emitting a single wavelength. Another possible diode laser is a tapered laser diode or tapered laser diode array. Tapered laser diodes function very much like standard laser diodes, but emit laser light of higher beam quality. Yet another possibility is to use a Master Oscillator Power Amplifier (MOPA) diode as a diode laser. MOPA diodes function to amplify initial signals while maintaining the same power density. The Master Oscillator portion serves to modulate the output wavelength of the laser diode by varying its input current. This modulation allows for selection of the wavelength over a range of about 30 nm.

There are several embodiments for making large adjustments to the wavelength emitted by the laser system. In one embodiment, a single laser diode cartridge 140 is inserted into the base unit and used for the desired period and then it is removed from the base unit through cartridge hatch 142 and replaced by a diode cartridge of another wavelength. In another embodiment, multiple cartridges emitting different wavelengths are contained in the base unit simultaneously. The cartridges are then selectively activated at separate times to operate at different wavelengths. Cartridge selection is by means of computer/controller. Another embodiment involving multiple cartridges allows for two or more wavelengths to be emitted simultaneously by simultaneously powering selected cartridges while they are attached to the base unit.

EXAMPLE 2

Laser diode cartridge A has an operating wavelength of 630 nm. The radiation procedure with cartridge A is completed and the cartridge is then replaced by cartridge B, which has an operating wavelength of 680 nm. Power is supplied and light is emitted at the new wavelength.

EXAMPLE 3

Laser diode cartridges A, B and C have operating wavelengths of 630 nm, 680 nm and 720 nm respectively and all three are contained in the base unit. Cartridge B is selected by means of a computer/controller on the outside of the base unit. The output of the system is 680 nm. Power to cartridge B is disconnected and cartridge C is selected. The output of the system is then 720 nm.

EXAMPLE 4

Laser diode cartridges A (630 nm), B (680 nm) and C (720 nm) are all contained in the base unit. The user selects all three cartridges by means of a computer/controller. Output from the three cartridges is combined into one fiber using a combiner as described in U.S. Pat. No. 5,668,903. Power is supplied and the system has an output of light at three different wavelengths.

Yet another multiple cartridge embodiment provides for multiple cartridges of the same wavelength to be contained in the base unit. In this case, multiple cartridges could be electrically powered simultaneously to boost laser power. This can provide a solution to the problem of wavelengths for which high power diode lasers are not presently available, but are needed for medical applications. If, however, longevity and not power is the goal of the system user, all of the diode cartridges can be powered at a fraction of full power, creating built-in redundancy. Such a system would not only have the advantage of longevity but also the advantage of low down time. Medical procedures can be completed safely without necessitating down time for repairs when a diode cartridge fails. This feature could prove quite crucial with regard to PDT procedures where there is a limited window of time during which the therapy will be effective.

EXAMPLE 5

An output power of 3 Watts at 630 nm is desired. It is not possible to generate the entire 3 W using one laser diode. Therefore, a diode laser system containing two diode cartridges is used. Each cartridge is simultaneously powered at full power and each cartridge emits 1½ W of laser power. Emissions from the two cartridges are combined in a combiner subsystem into a single output source. The combined output of the laser system is 3 Watts.

EXAMPLE 6

A diode laser system consists of two diode cartridges of the same wavelength contained in a base unit. Both cartridges are operating at ½ power. Then, when one cartridge fails, it is shut off and the remaining cartridge is increased to full power. In this way, the laser may produce a steady output despite diode failure. The working cartridge then continues to operate until the medical procedure is complete and the malfunctioning diode cartridge is replaced.

Several other variations are possible without deviating from the spirit of the invention. Instead of using optical connection 116 to link optical port 114 to treatment fiber 136 as mentioned above, in another embodiment, the optical port 114 of the cartridge is coupled directly with treatment fiber 136. In this case, suitable shutter means need to be incorporated into the cartridge for laser safety reasons.

Although this invention relates primarily to laser diodes as diode light sources, other diode light sources may be possible for PDT applications. Standard Light Emitting Diodes (LEDs), however, are not suitable for this application because the wavelength output range of 50–100 nm Full Width Half Maximum (FWHM) is too broad. Standard LEDs are also unacceptable for PDT because generally their power level is too low. SuperLuminescent Diodes (SLDs) have an FWHM of about 25 nm which is two to four times narrower than that for LEDs. Thus, the use of SLDs may be acceptable for PDT applications. Though SLDs emit a lower power light than lasers, they emit a much stronger light than LEDs. SLD light of this power is suitable for PDT applications. If more power were needed, the power could be increased using multiple diode cartridges, as was described in example 5 above. Laser diodes are the preferred light source because of their power and because they possess a FWIM of only 1–2 nm.

EXAMPLE 7

The present invention may also be used in PDT treatment of macular degeneration of the eye. Drug identification scanner 144 scans drug bar code and relays activation wavelength information to computer/controller 132. Computer/controller 132 surveys the diode cartridges contained in the base unit to determine if a cartridge of the appropriate wavelength is available. Upon finding appropriate cartridge B, computer/controller 132 selectively powers cartridge B. Computer/controller 132 also contains data pertaining to the size and NA of treatment fiber 136 and regulates power supplied to cartridge B accordingly, so that radiation of the proper energy density is emitted at the output end of treatment fiber 136. Additionally, slit lamps (not shown) may be used for radiation entry into the eye. Slit lamps adjust the spot size over the area to be treated and therefore can change the emitted energy density from what exits the treatment fiber. Thus, a danger exists that a slit lamp can make the emitted energy density too great for a given wavelength and operation. Therefore, as a safety mechanism, the system is equipped with a means to measure the power density leaving the slit lamp using a feedback loop. Measured power density is displayed on the display screen of computer/controller 132. If the measured power density exceeds certain limits for the given application then the power to the system is shut down. By this safety mechanism, accidental radiation overdoses to the eye may be prevented.

Other options involve devices similar to slit lamps which process the light beyond the fiber. Such devices could have their operation integrated into the system as well if safety mechanisms were in place.

Figure 2:
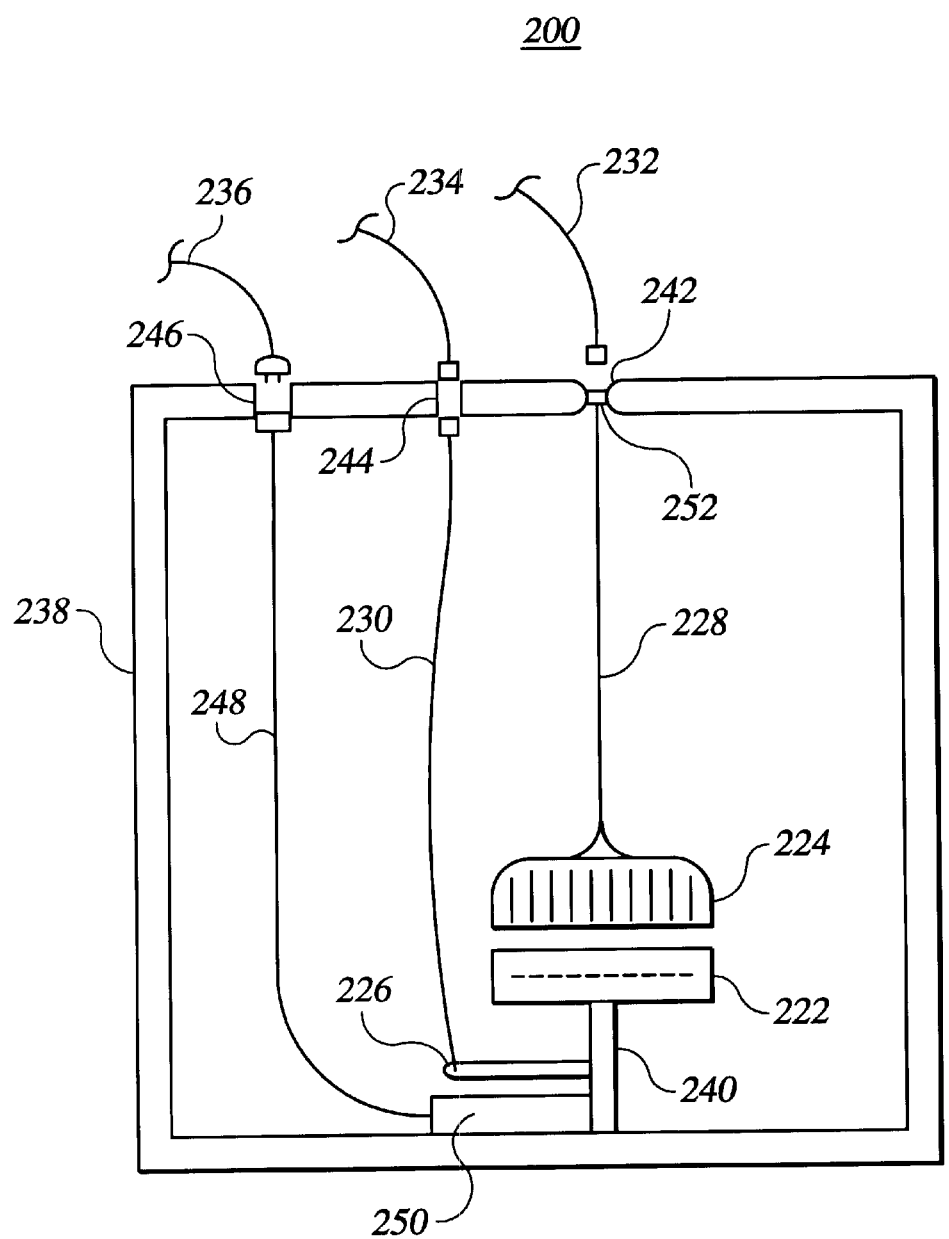
FIG. 2 is a top view of a diode cartridge which can be inserted into the base unit of the system.

The application of the disclosed cartridge principle may be useful for disciplines other than PDT. Some surgical procedures are more effective at wavelengths beyond the 630 nm to 800 nm range. For example, cutting and coagulation are best performed at other wavelengths. Other medical applications such as sensing of blood gas and hematocrit levels would have their own preferred operating wavelengths to get optimum sensing response Shown in FIG. 2 is diode cartridge 200.

Diode array 222 is mounted on diode support structure 240. Diode array 222 is coupled with fiber optic array 224, within cartridge 200. Fiber optic array 224 may be a planar wave-guide combiner as described in U.S. Pat. No. 5,668,903. Fiber optic array 224 passes light into fiber optic cable 228 which connects to optical connector 232 immediately outside the surface of the cartridge at optical port 242. Optical port may have an optional lens 252 to focus the output beam. Data/Identification connection 226 is joined to diode structure 240 and transmits data into data/identification cable 230 which connects to data/identification connector 234 at data/identification port 244. Electrical connection 236 joins with electrical cable 248 at electrical port 246. Electrical cable 248 transmits current to wiring panel 250 at the base of diode support structure 240.

Figure 3:
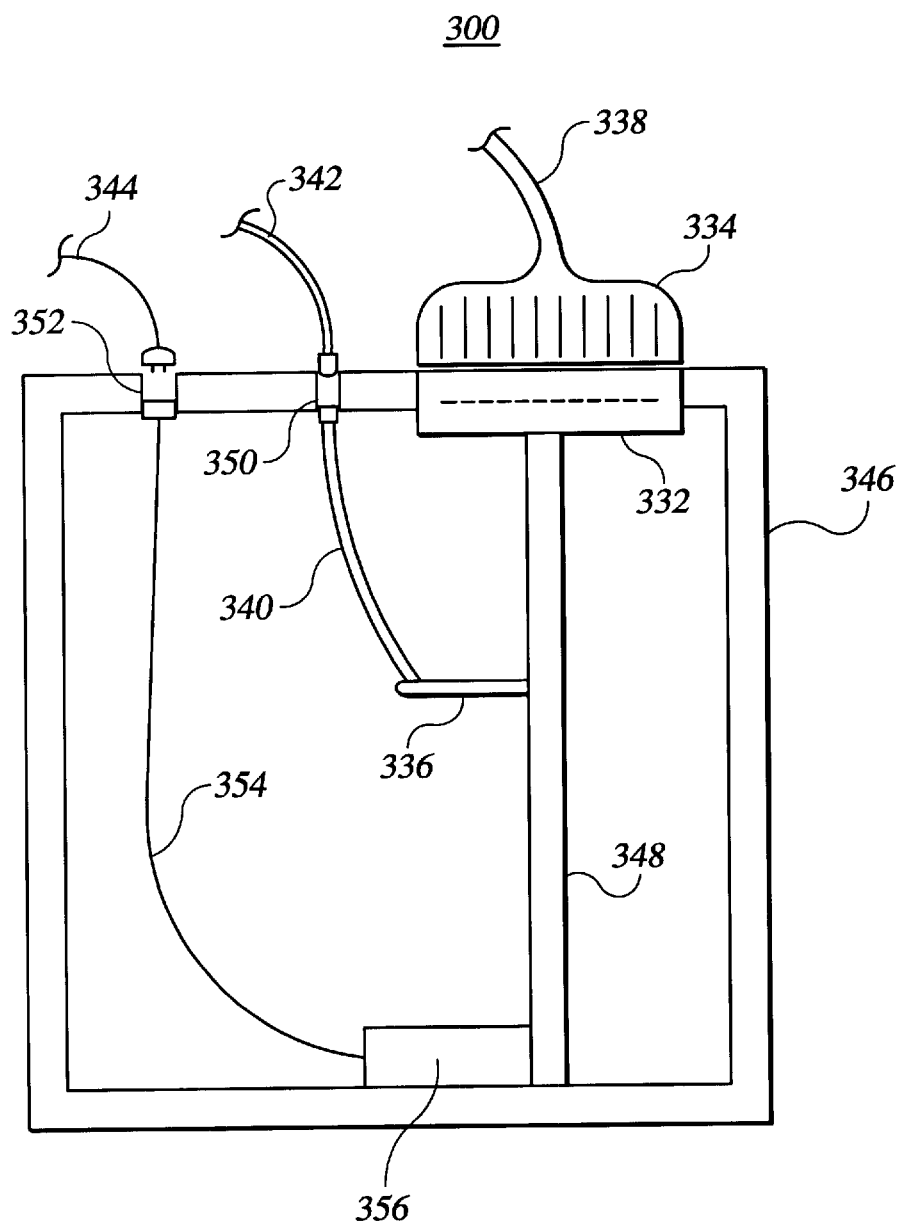
FIG. 3 is an alternate design of diode cartridge with external diode/fiber coupling.

Shown in FIG. 3 is alternate diode cartridge configuration 300.

Diode array 332 is mounted on diode support structure 348. Unlike in 200, where coupling is internal to the cartridge, diode array 332 is coupled with fiber optic array 334, on the outer surface of the cartridge 346. Fiber optic array 334 passes light to optical connector 338. Data/Identification connection 336 is joined to diode support structure 348 and transmits data into data/identification cable 340 which connects to data/identification connector 342 at data/identification port 350. Electrical connection 344 joins with electrical cable 354 at electrical port 352. Electrical cable 354 transmits current to wiring panel 356 at the base of diode support structure 348.

Figure 4:
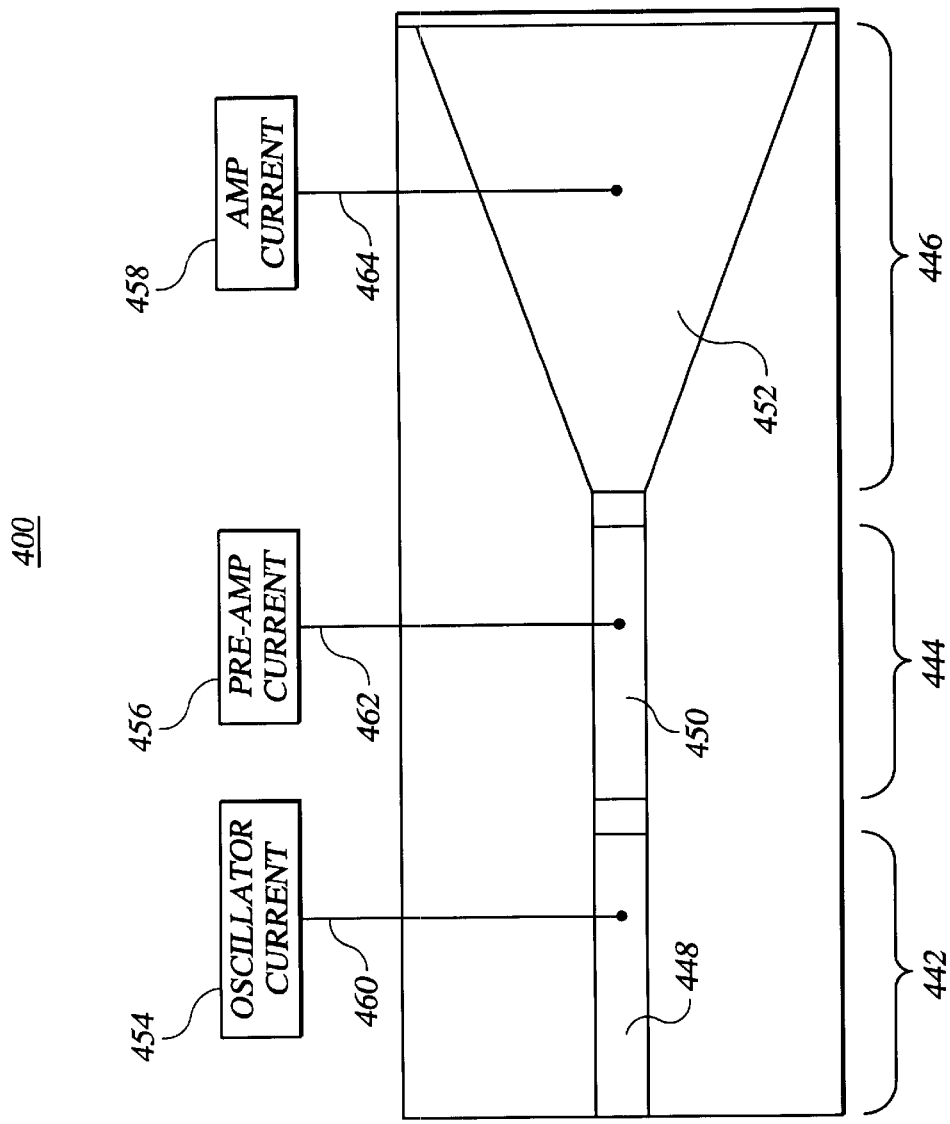
FIG. 4 is a schematic drawing of a Master Oscillator Power Amplifier suitable for use within the present invention.

Shown in FIG. 4 is a variant of a Master Oscillator Power Amplifier (MOPA). A MOPA generally comprises two sections namely a master oscillator section 442 and a power amplifier section 446. Variant MOPA 400 comprises three sections, namely a master oscillator or laser generating section 442, an optional pre-amplifier or control section 444, and an amplifier section 446. Current is transmitted to sections 442, 444, and 446 at conductive 448, 450 and 452, respectively. Stripe 448 is coupled with oscillator current source 454 by way of line 460. Stripe 450, which preferably has the same width as stripe 448, is coupled with pre-amplifier current source 456 by way of line 462. Stripe 452, the width of which expands relative to the width of stripes 448 and 450, is coupled with an amplifier current source 458 by way of line 464. U.S. Pat. No. 5,175,643, "Monolithic Integrated Master Oscillator Power Amplifier", invented by John R. Andrews and assigned to Xerox Corporation, discloses a similar design which could also function a diode laser source for the present invention.

Having described preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A tunable diode laser system comprising:
   at least one interchangeable diode laser cartridge, at least one optical treatment element and a base unit;
   said at least one interchangeable diode laser cartridge comprises:
      at least one diode laser having an optical output of a desired wavelength,
      an optical port, optically connected to said at least one diode laser, and
      means for identifying and communicating a set of laser diode cartridge operating parameters to said base unit;
   said at least one optical treatment element comprising:
      a proximal end that connects to said base unit,
      a distal end which delivers said optical output to a treatment site, and means to deliver said optical output from said proximal end to a said distal end;
   said base unit substantially comprises
      an enclosure,
      an electrical power supply,
      a system controller having means to identify said optical treatment element and means to calculate energy and energy density at a distal end of said optical treatment element,
      an output terminal to which said proximal end of said optical treatment element connects,
      means for controlling and dissipating heat,
      means for connecting said at least one interchangeable diode laser cartridge to said base unit,
      means for selecting a desired output wavelength and a power output from said at least one interchangeable diode laser cartridge,
      means for electrical connections to connect said electrical power supply to said at least one interchangeable diode laser cartridge,
      means for optical connection to transfer said optical output from said optical port in said cartridge to said output terminal protruding through said enclosure, where said at least one optical treatment element connects to said base unit;
      means for controlling and dissipating heat to maintain a desired temperature of said base unit and said at least one interchangeable diode laser cartridge; and
      wherein said optical output is tuned to a desired wavelength by selecting said at least one interchangeable diode laser cartridge having an optical output of about said desired wavelength and controlling said temperature to make wavelength adjustment to said optical output.

2. A tunable diode laser system according to claim 1, wherein said diode laser is selected from a group consisting of laser diodes, laser diode arrays, Master Oscillator Power Amplifier (MOPA) diodes, diode pumped fiber lasers, super luminescent diodes and tapered laser diodes.

3. A tunable diode laser system according to claim 1, wherein said at least one interchangeable diode laser cartridge is a plurality of interchangeable diode laser cartridges and where said system further comprises an optical combiner that optically connects and combines output from said plurality of interchangeable diode laser cartridges into said means for optical connection.

4. A tunable diode laser system according to claim 3, wherein each said interchangeable diode laser cartridge of said plurality of cartridges is selected to operate at a different wavelength than other said interchangeable diode laser cartridges in said system.

5. A tunable diode laser system according to claim 3, wherein at least two said interchangeable diode laser cartridges of said plurality of cartridges operate at a same selected wavelength.

6. A tunable diode laser system according to claim 3, wherein at least two interchangeable diode laser cartridges of said plurality of diode laser cartridges are powered simultaneously.

7. A tunable diode laser system according to claim 1 further comprising means for inputting information on identity and properties of a photoactivatible drug into said controller; wherein and said means for selecting a desired output wavelength and power output within said base unit makes selections based upon said inputted information on said identity and properties of said photoactivatible drug.

8. A tunable diode laser system according to claim 7, wherein said means for inputting information on identity and properties of a photoactivatible drug into said controller is a bar code reader which communicates to said controller; and whereby a bar code label that contains said information and accompanies said photoactivatible drug is read and said information on identity and properties of said photoactivatible drug is inputted into said controller.

9. A tunable diode laser system according to claim 1, further comprising:
   means within said base unit to identify ancillary equipment that modifies optical outputs from said laser system, including energy and energy density of said signal;
   feedback means for said base unit to monitor changes in said optical output caused by said ancillary equipment; and
   means for said controller within said base unit to display changes in said optical output properties.

10. A tunable diode laser system according to claim 1, wherein said optical treatment element comprises an optical fiber.

11. A tunable diode laser system according to claim 3, wherein said optical combiner comprises a planar waveguide.

12. A tunable diode laser system according to claim 1, wherein said at least one interchangeable diode laser cartridge further comprises at least two diode lasers and an optical combiner element to combine output from said at least two diode lasers into one optical output at said optical port.

* * * * *